United States Patent [19]

Hanson et al.

[11] Patent Number: 4,496,663
[45] Date of Patent: Jan. 29, 1985

[54] PRODUCTION OF CATALYSTS

[75] Inventors: Charles B. Hanson; Colin R. Harrison, both of Guisborough, England

[73] Assignee: Imperial Chemical Industries PLC, United Kingdom

[21] Appl. No.: 505,820

[22] Filed: Jun. 20, 1983

[30] Foreign Application Priority Data

Jun. 29, 1982 [GB] United Kingdom ................. 8218709

[51] Int. Cl.$^3$ ........................ B01J 27/14; B01J 23/16; B01J 21/00
[52] U.S. Cl. .................................... 502/209; 502/105; 502/312; 502/350
[58] Field of Search ............... 502/105, 209, 312, 350; 423/305

[56] References Cited

U.S. PATENT DOCUMENTS

| | | | |
|---|---|---|---|
| 3,342,847 | 9/1967 | Kruse | 502/350 X |
| 3,926,848 | 12/1975 | Wristers et al. | 502/105 |
| 3,951,858 | 4/1976 | Schick et al. | 502/105 |
| 3,998,876 | 12/1976 | Kato et al. | 252/435 |
| 4,051,179 | 9/1977 | Sonobe et al. | 502/209 X |
| 4,061,857 | 12/1977 | Kuroda et al. | 502/105 X |
| 4,170,570 | 10/1979 | Zogata et al. | 502/312 |
| 4,209,423 | 6/1980 | Hutchings et al. | 502/209 |
| 4,222,945 | 9/1980 | Higgins et al. | 502/209 X |
| 4,225,465 | 9/1980 | Bremer | 502/209 |
| 4,305,843 | 12/1981 | Krobetz et al. | 502/209 X |
| 4,359,407 | 11/1982 | Dolhyj et al. | 502/209 |

Primary Examiner—William G. Wright
Attorney, Agent, or Firm—Cushman, Darby & Cushman

[57] ABSTRACT

Mixed oxide catalyst precursors are milled in the substantial absence of liquid to mean crystallite sizes of at most 1,000Å and formed into catalyst pellets. The process is particularly suitable in the production of vanadium/phosphorus mixed oxide catalysts for the oxidation of butane to maleic anhydride.

. 5 Claims, No Drawings

PRODUCTION OF CATALYSTS

This invention relates to the production of catalysts.

In our British Patent Application No. 2,019,839 we have disclosed catalysts for the production of carboxylic acid anhydrides which are produced from catalyst precursors having a mean crystallite size of at most 1,000 Å. Crystallites of such size were disclosed as being produced by ball milling in the presence of a suitable solvent for example an aliphatic hydrocarbon.

We have found that mixed oxide oxidation catalysts especially those suitable for the oxidation of hydrocarbons to carboxylic acid anhydrides, for example the oxidation of $C_4$ hydrocarbons especially n-butane and/or the n-butenes to maleic anhydride, may very effectively be milled in the substantial absence of liquid. By operating in this way the flammability hazard associated with organic solvents may be avoided and we have surprisingly found that the milling is more effective in the absence of such liquids than in their presence. Furthermore whereas, in general, milling aids, for example cationic surfactants are advantageous when an organic liquid is present, such milling aids are unnecessary when the catalyst is milled dry, though they may be included if desired, especially if like cetyl trimethyl ammonium bromide they assist in a subsequent pelleting stage.

The invention therefore comprises a process in which a mixed oxide oxidation catalyst precursor is milled in the substantial absence of liquid until its mean crystallite size is at most 1,000 Å and preferably at most 500 Å and is then formed into catalyst pellets. The pellets may be formed for example by extrusion. They may be used in a fixed bed reaction or if desired, crushed and used in a fluidised bed reactor.

By mixed oxide reaction catalyst precursor we include mixed oxide particles which themseleves possess catalytic properties or which may be converted to a catalytically active form by heating, oxidation, reduction or other physical or chemical treatment.

It is preferred that the milling should be ball milling.

The catalysts produced may be vanadium/molybdenum mixed oxide catalysts which are suitable for example, for the oxidation of benzene to maleic anhydride, vanadium/titanium mixed oxide catalysts for example those suitable for the oxidation of ortho-xylene to phthalic anhydride or vanadium/phosphorus mixed oxide catalysts which are suitable for example for the oxidation of $C_4$ linear hydrocarbons as aforesaid to maleic anhydride. Suitably the ratio of vanadium to phosphorus in such catalysts is in the range 0.5:1 to 2:1 and preferably 0.7:1 to 1.2:1.

A particularly suitable mixed oxide oxidation catalyst precursor is vanadium/phosphorus mixed oxide in the phase A, phase X (a form of $\alpha VOPO_4$) or phase B form. In these the valency of the vanadium is in the range 4 to 5. Phase X is described by Jordan and Calvo in Canadian Journal of Chemistry 51 2621-5 (1973). Phase B is disclosed in U.S. Pat. No. 3,864,280; it has a characteristic powder X-ray diffraction pattern using copper $K\alpha$ radiation as follows.

| d (Angstrom) | Line position 2θ Degrees | Intensity, I |
|---|---|---|
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

Phase A has a characteristic powder X-ray diffraction pattern using copper $K\alpha$ radiation as follows.

| d (Angstrom) | Line position 2θ Degrees | Intensity, I |
|---|---|---|
| 5.7 | 15.6 | 10 |
| 4.5 | 19.7 | 2 |
| 3.7 | 24.3 | 2 |
| 3.3 | 27.1 | 2 |
| 3.1 | 28.7 | <1 |
| 2.9 | 30.5 | 2 |
| 2.8 | 32.1 | 1 |
| 2.7 | 33.8 | <1 |

The relative intensities vary with the method of preparation and the V:P ratio.

Suitably at least 30% and preferably at least 50% of a vanadium/phosphorus mixed oxide catalyst precursor is phase A, B and/or X.

The process of this invention is particularly applicable in the production of the catalysts disclosed in British Patent Application No. 2,019,839 and British Pat. No. 1,601,121.

Catalysts produced according to the invention are suitably formed into pellets which are shaped as rings or hollow cylinders. In general they tend to possess greater strength when formed into pellets of mechanically vulnerable shape than corresponding pellets prepared from unmilled precursors. They suitably have surface areas of at least 7, and preferably at least 10, for example 10 to 75 $m^2/g$. They may if desired be promoted by incorporating in them before, during or after the milling and/or pelleting stage promoters for example molybdenum, cobalt or lanthanum compounds.

EXAMPLE 1

A 10 liter milling pot was charged with a vanadium/phosphorus mixed oxide precursor produced according to U.S. Pat. No. 4,209,423 Example 2 (1,400 g, mean crystallite size 5μ) and 3,500 ml of high density 4 mm to 25 mm diameter alumina balls. The precursor was predominantly phase A. The ratio of vanadium to phosphorus atoms was about 1:1.1 and the valency of the vanadium was in the range 4 to 4.5. After the pot had been rotated on rollers at 80 revs/min for 2 days the catalyst precursor was grey in colour and had a mean crystallite size of 250 Å.

The milled catalyst was mixed with 3% w/w of a commercially available pelleting aid sold under the trade name Sterotex and pressed into cylindrical pellets 4.5 mm diameter ×4.5 mm length, of pellet density 1.65 g/$cm^3$.

1,200 ml of the catalyst pellets were charged to a 360 cm long, 22 mm internal diameter tube reactor and activated by passing 1.5% butane in air over the catalyst at 370°–420° C. for 3 days. The activated catalyst had a surface area of 30 $m^2/g$ and gave the following performance with a feed of 1.5% butane in air at a gas hourly space velocity of 1,000:85% conversion at 371° C., 73% selectivity and 62% pass yield.

EXAMPLE 2 (COMPARATIVE)

Example 1 was repeated except that cyclohexane (2,400 ml) and cetyltrimethyl ammonium bromide (28 g) were also added to the milling pot.

After 10 days the catalyst precursor was grey-blue in colour and had a mean crystallite size of 750 Å.

After pelleting and activation as described in Example 1 the surface area was 25 m$^2$/g. When tested as described in Example 1 the performance at 386° C. was, 85% conversion, 70.5% selectivity and 60% pass yield.

EXAMPLE 3

Dry milled catalyst precursor as produced in Example 1 was pressed into hollow cylindrical pellets 4.5 mm in diameter ×4.5 mm in length with a 1.5 mm hole.

The density of the pellets (excluding the hole) was 1.65 g/cm$^3$. After activation the catalyst had a surface area of 29 m$^2$/g. The crush strength was: (vertical) 85 kg, and (horizontal) 8 kg.

The performance with a feed of 1.5% butane at a gas hourly space velocity of 1,000 at 381° C. was: 85% conversion, 75% selectivity and 64% pass yield.

We claim:

1. A process for producing a catalyst consisting essentially of a vanadium/phosphorus mixed oxide for the oxidation of butane to maleic anhydride, said process comprising the steps of milling a precursor of the mixed oxide catalyst in the substantial absence of liquid until the mean crystallite size of the catalyst precursor is at most 1000 Angstroms, and subsequently forming the milled catalyst precurosr into catalyst pellets.

2. A process as claimed in claim 1 in which the ratio of vanadium to phosphorus in the vandium/phosphorus mixed oxide is in the range 0.7:1 to 1.2:1.

3. A process as claimed in claim 2 in which the valency of the vanadium in the vandium/phosphorus mixed oxide is in the range 4 to 5.

4. A process as claimed in claim 1 in which at least 30% of the vanadium/phosphorus mixed oxide is present as phase A, phase X and/or phase B.

5. A process as claimed in claim 1 in which the catalyst precursor is milled until its mean crystallite size is at most 500 Å.

* * * * *